US009877634B2

(12) United States Patent
Takei

(10) Patent No.: US 9,877,634 B2
(45) Date of Patent: Jan. 30, 2018

(54) IMAGE PROCESSING SYSTEM AND IMAGE PROCESSING APPARATUS

(71) Applicant: OLYMPUS CORPORATION, Tokyo (JP)

(72) Inventor: Shunji Takei, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/269,015

(22) Filed: Sep. 19, 2016

(65) Prior Publication Data

US 2017/0007097 A1   Jan. 12, 2017

Related U.S. Application Data

(63) Continuation of application No. PCT/JP2015/056053, filed on Mar. 2, 2015.

(30) Foreign Application Priority Data

Jun. 2, 2014   (JP) ................................. 2014-114357

(51) Int. Cl.
  *A61B 1/00*   (2006.01)
  *G02B 23/24*   (2006.01)
  (Continued)

(52) U.S. Cl.
  CPC ...... *A61B 1/00009* (2013.01); *A61B 1/00004* (2013.01); *A61B 1/00172* (2013.01);
  (Continued)

(58) Field of Classification Search
  CPC ............ A61B 1/00004; A61B 1/00009; A61B 1/00172; A61B 1/04; A61B 1/06; G02B 23/2469; G02B 23/26
  See application file for complete search history.

(56) References Cited

U.S. PATENT DOCUMENTS

2007/0109557 A1 *  5/2007  Saito ................. G01B 11/0608
                                                      356/602
2013/0155215 A1 *  6/2013  Shimada ............ A61B 1/00172
                                                       348/68
(Continued)

FOREIGN PATENT DOCUMENTS

EP      2 803 312 A1    11/2014
JP      61-48333 A       3/1986
(Continued)

OTHER PUBLICATIONS

International Search Report dated May 26, 2015 issued in PCT/JP2015/056053.
(Continued)

*Primary Examiner* — Md Haque
*Assistant Examiner* — Nazmul Haque
(74) *Attorney, Agent, or Firm* — Scully, Scott, Murphy & Presser, P.C.

(57) ABSTRACT

An image processing system includes: a light source portion configured to emit illuminating light to be radiated to an object; a light receiving optical member for guiding return light from the object: a light detecting portion configured to receive the return light caused to be incident through the light receiving optical member to generate an electric signal, amplify the generated electric signal, convert the amplified electric signal to a digital signal and output the digital signal; an image processing portion configured to generate an image based on the digital signal outputted from the light detecting portion and perform gain adjustment for the generated image; and a parameter adjusting portion configured to adjust a predetermined parameter based on a variable range of an output value of the light source portion and a variable range of a gain value in the gain adjustment.

10 Claims, 6 Drawing Sheets

(51) Int. Cl.
*A61B 1/04* (2006.01)
*A61B 1/06* (2006.01)
*G02B 23/26* (2006.01)

(52) U.S. Cl.
CPC .................. *A61B 1/04* (2013.01); *A61B 1/06* (2013.01); *G02B 23/2469* (2013.01); *G02B 23/26* (2013.01)

(56) References Cited

U.S. PATENT DOCUMENTS

2013/0345508 A1* 12/2013 Akui ................. A61B 1/00172
600/109

2014/0300718 A1* 10/2014 Krattiger .............. H04N 5/2354
348/68

FOREIGN PATENT DOCUMENTS

| | | |
|---|---|---|
| JP | 2007-143624 A | 6/2007 |
| JP | 2013-202167 A | 10/2013 |
| JP | 2013202167 | * 10/2013 |
| JP | 5363688 B1 | 12/2013 |
| WO | WO 2012/132754 A1 | 10/2012 |
| WO | WO 2013/105329 A1 | 7/2013 |

OTHER PUBLICATIONS

Japanese Office Action dated Mar. 8, 2016 issued in JP 2015-558686.

\* cited by examiner

IMAGE PROCESSING SYSTEM AND IMAGE PROCESSING APPARATUS

CROSS REFERENCE TO RELATED APPLICATION

This application is a continuation application of PCT/JP2015/056053 filed on Mar. 2, 2015 and claims benefit of Japanese Application No. 2014-114357 filed in Japan on Jun. 2, 2014, the entire contents of which are incorporated herein by this reference.

BACKGROUND OF INVENTION

1. Field of the Invention

The present invention relates to an image processing system and an image processing apparatus, and more particularly to an image processing system and an image processing apparatus which scans an object to acquire an image.

2. Description of the Related Art

For endoscopes in a medical field, various techniques for reducing a diameter of an insertion portion to be inserted into a body cavity of a subject are proposed in order to reduce a burden on the subject. As examples of such techniques, a scanning type endoscope which does not have a solid image pickup device on a part corresponding to the insertion portion described above, a scanning type endoscope system configured being provided with the scanning type endoscope, and the like are known.

More specifically, the scanning type endoscope system described above is configured, for example, to two-dimensionally scan an object in a scan pattern set in advance by causing a distal end portion of an illumination fiber configured to guide illuminating light emitted from a light source to be swung, receive return light from the object by a light receiving fiber arranged around the illumination fiber, and generate an image of the object based on the return light received by the light receiving fiber. As what has a configuration similar to that of such a scanning type endoscope system, for example, a scanning endoscope apparatus disclosed in Japanese Patent No. 5363688 is known.

SUMMARY OF THE INVENTION

An image processing system of an aspect of the present invention includes: a light source portion configured to emit illuminating light to be radiated to an object; a light receiving optical member for guiding return light from the object to which the illuminating light is radiated; a light detecting portion configured to receive the return light caused to be incident through the light receiving optical member to generate an electric signal, amplify the generated electric signal, convert the amplified electric signal to a digital signal and output the digital signal; an image processing portion configured to generate an image based on the digital signal outputted from the light detecting portion and perform gain adjustment for the generated image; and a parameter adjusting portion configured to adjust a predetermined parameter in a process until the digital signal is outputted from the light detecting portion after the return light passing through the light receiving optical member is caused to be incident on the light detecting portion, based on a variable range of an output value of the light source portion and a variable range of a gain value in the gain adjustment by the image processing portion.

An image processing apparatus of an aspect of the present invention includes: a light detecting portion configured to receive return light caused to be incident through a light receiving optical member to generate an electric signal, amplify the generated electric signal, convert the amplified electric signal to a digital signal and output the digital signal; an image processing portion configured to generate an image based on the digital signal outputted from the light detecting portion and perform gain adjustment for the generated image; and a parameter adjusting portion configured to adjust a predetermined parameter in a process until the digital signal is outputted from the light detecting portion after the return light passing through the light receiving optical member is caused to be incident on the light detecting portion, based on a variable range of an output value of the light source portion and a variable range of a gain value in the gain adjustment by the image processing portion.

DETAILED DESCRIPTION OF THE PREFERRED EMBODIMENT(S)

Embodiments of the present invention will be described below with reference to drawings.

First Embodiment

Figure 1:
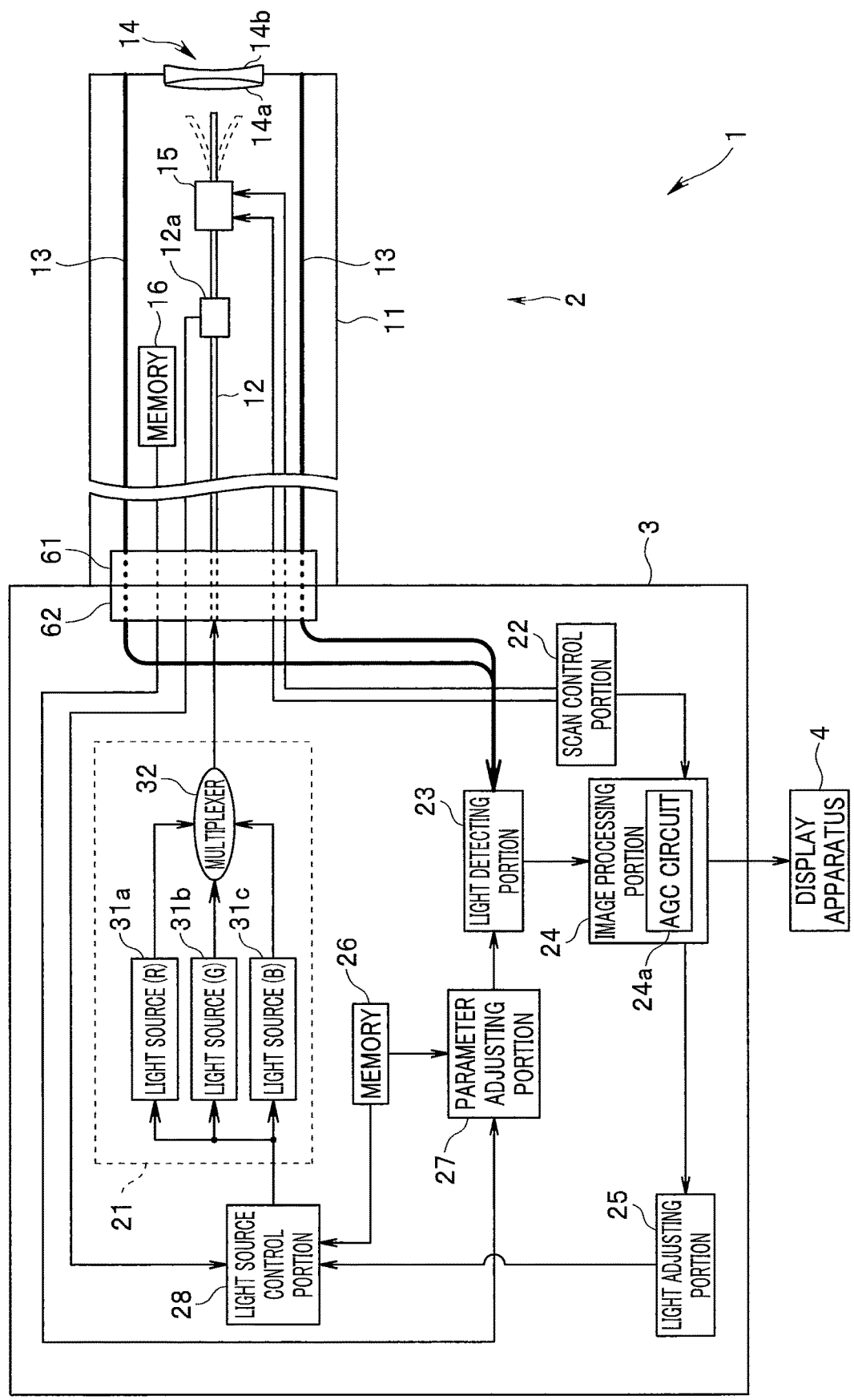
FIG. 1 is a diagram showing a configuration of main portions of an endoscope system according to a first embodiment.

FIGS. 1 to 4 relate to a first embodiment of the present invention. FIG. 1 is a diagram showing a configuration of main portions of an endoscope system according to the first embodiment.

For example, as shown in FIG. 1, an endoscope system 1 is configured having a scanning-type endoscope 2 to be inserted into a body cavity of a subject, a body apparatus 3 to which the endoscope 2 can be connected, and a display apparatus 4 to be connected to the body apparatus 3.

The endoscope 2 is configured having an insertion portion 11 which is formed being provided with an elongated shape insertable into a body cavity of a subject and flexibility.

A proximal end portion of the insertion portion 11 is provided with a connector portion 61 for detachably connecting the endoscope 2 to a connector receiving portion 62 of the body apparatus 3.

An electrical connector device for electrically connecting the endoscope 2 and the body apparatus 3 is provided inside the connector portion 61 and the connector receiving portion 62, though it is not shown. Further, an optical connector device for optically connecting the endoscope 2 and the body apparatus 3 is provided inside the connector portion 61 and the connector receiving portion 62, though it is not shown.

On the other hand, through a part from the proximal end portion to a distal end portion inside the insertion portion 11, each of an illumination fiber 12 for guiding light supplied from the body apparatus 3 to a condensing optical system 14 and one or more light receiving fibers 13 for receiving return light (hereinafter also referred to as reflected light) from an object and guiding the return light to the body apparatus 3 is inserted.

An incident end portion of the illumination fiber 12, including a light incident surface, is arranged inside the connector portion 61. Further, an end portion of the illumination fiber 12, including a light emitting surface, is arranged in a vicinity of a light incident surface of a lens 14a provided on the distal end portion of the insertion portion 11.

A light amount detecting portion 12A is provided on a midway portion of the illumination fiber 12 inside the insertion portion 11.

The light amount detecting portion 12A is configured being provided with, for example, an optical divider and a photo diode. Further, the light amount detecting portion 12A is configured to detect an amount of light which passes through the illumination fiber 12, generate a light amount detection signal corresponding to the detected amount of light and output the light amount detection signal to the body apparatus 3.

Note that the light amount detecting portion 12A is not limited to such that is provided inside the insertion portion 11 but may be provided in a vicinity of the connector receiving portion 62 inside the body apparatus 3, for example, if fluctuation in the amount of light by connection of the connector portion 61 and the connector receiving portion 62 is difficult to occur.

An incident end portion of the light receiving fiber 13, including a light incident surface, is fixedly arranged on a circumference of a light emitting surface of a lens 14b on a distal end surface of the distal end portion of the insertion portion 11. Further, an emission end portion of the light receiving fiber 13, including a light emitting surface, is arranged inside the connector portion 61.

That is, according to the configuration as described above, when the endoscope 2 and the body apparatus 3 are connected, light emitted from the body apparatus 3 is caused to be incident on the light incident surface of the illumination fiber 12 provided in the connector portion 61. Further, according to the configuration as described above, when the endoscope 2 and the body apparatus 3 are connected, light incident from the light incident surface of the light receiving fibers 13 is emitted to the body apparatus 3 via the connector portion 61 and the connector receiving portion 62.

The condensing optical system 14 is configured having the lens 14a on which light passing through the light emitting surface of the illumination fiber 12 is caused to be incident, and the lens 14b from which the light passing through the lens 14a is emitted to an object.

On the midway portion of the illumination fiber 12 on the distal end portion side of the insertion portion 11, an actuator portion 15 is provided which is configured to be capable of causing an emission end portion of the illumination fiber 12 to be swung, by being driven based on a drive signal supplied from a scan control portion 22 of the body apparatus 3.

The actuator portion 15 is configured being provided with, for example, a first actuator provided with one or more piezoelectric elements capable of causing the emission end portion of the illumination fiber 12 to be swung along a first direction, by being driven based on a drive signal supplied from the scan control portion 22 of the body apparatus 3, and a second actuator provided with one or more piezoelectric elements capable of causing the emission end portion to be swung in a second direction orthogonal to the first direction, by being driven based on a drive signal supplied from the scan control portion 22 of the body apparatus 3.

Inside the insertion portion 11, a memory 16 is provided in which optical characteristic information including a transmittance T1 of the illumination fiber 12 provided in the endoscope 2, light receiving efficiency Le set for each model of endoscope 2, and a transmittance T2 of the light receiving fibers 13 provided in the endoscope 2 is stored. The optical characteristic information stored in the memory 16 is read out by a parameter adjusting portion 27 of the body apparatus 3 when the connector portion 61 of the endoscope 2 and the connector receiving portion 62 of the body apparatus 3 are connected.

The transmittance T1 is set, for example, as a dimensionless value between 0 and 1, including 0 and 1, according to a length of the illumination fiber 12. Further, the transmittance T1 is set as a value corresponding to each wavelength band of light supplied from the body apparatus 3, that is, a value corresponding to each of R light, G light and B light to be described later.

The light receiving efficiency Le is calculated, for example, as a value of a ratio of an amount of the reflected light of a predetermined wavelength band, which is received by the light receiving fibers 13 and an amount of the light of the predetermined wavelength band emitted from the condensing optical system 14 in a case where the light of the predetermined wavelength band is radiated to a predetermined object arranged at a standard observation distance which differs for each model of endoscope 2. Further, the light receiving efficiency Le is set as a value corresponding to each wavelength band of light supplied from the body apparatus 3, that is, a value corresponding to each of the R light, the G light and the B light to be described later.

Note that the standard observation distance described above is defined, for example, as such a distance that a contrast value of an image obtained by scanning an object is equal to or larger than a predetermined value. Further, the model of endoscope 2 is defined, for example, as such that differs according to application sites of a living body, such as a respiratory organ and a digestive organ.

The transmittance T2 is set, for example, as a dimensionless value between 0 and 1, including 0 and 1, according to a length and the number of the light receiving fibers 13. Further, the transmittance T2 is set as a value corresponding to each wavelength band of light supplied from the body apparatus 3, that is, a value corresponding to each of the R light, the G light and the B light to be described later.

The body apparatus 3 is configured having a light source portion 21, the scan control portion 22, a light detecting portion 23, an image processing portion 24, a light adjusting portion 25, the memory 26, the parameter adjusting portion 27 and a light source control portion 28.

The light source portion 21 is configured having a light source 31a, a light source 31b, a light source 31c and a multiplexer 32.

The light source 31a is provided with, for example, a laser light source and configured to be switched between an on state and an off state in response to control of the light source control portion 28. Further, the light source 31a is configured to generate light of a red wavelength band (hereinafter also referred to as R light) with an output value corresponding to control of the light source control portion 28 when the light source 31a is in the on state.

The light source 31b is provided with, for example, a laser light source and configured to be switched between the on state and the off state in response to control of the light source control portion 28. Further, the light source 31b is configured to generate light of a green wavelength band (hereinafter also referred to as G light) with an output value corresponding to control of the light source control portion 28 when the light source 31b is in the on state.

The light source 31c is provided with, for example, a laser light source and configured to be switched between the on state and the off state in response to control of the light source control portion 28. Further, the light source 31c is configured to generate light of a blue wavelength band (hereinafter also referred to as B light) with an output value corresponding to control of the light source control portion 28 when the light source 31c is in the on state.

The multiplexer 32 is configured to be capable of emitting a white color light obtained by multiplexing the R light emitted from the light source 31a, the G light emitted from the light source 31b and the B light emitted from the light source 31c, to the light incident surface of the illumination fiber 12 provided in the connector receiving portion 62.

The scan control portion 22 is configured being provided with, for example, a signal generator. Further, the scan control portion 22 is configured to generate a drive signal for causing the emission end portion of the illumination fiber 12 to be swung in a predetermined scan pattern such as a spiral shape and a lissajous shape and output the generated drive signal to the actuator portion 15 and the image processing portion 24.

Figure 2:
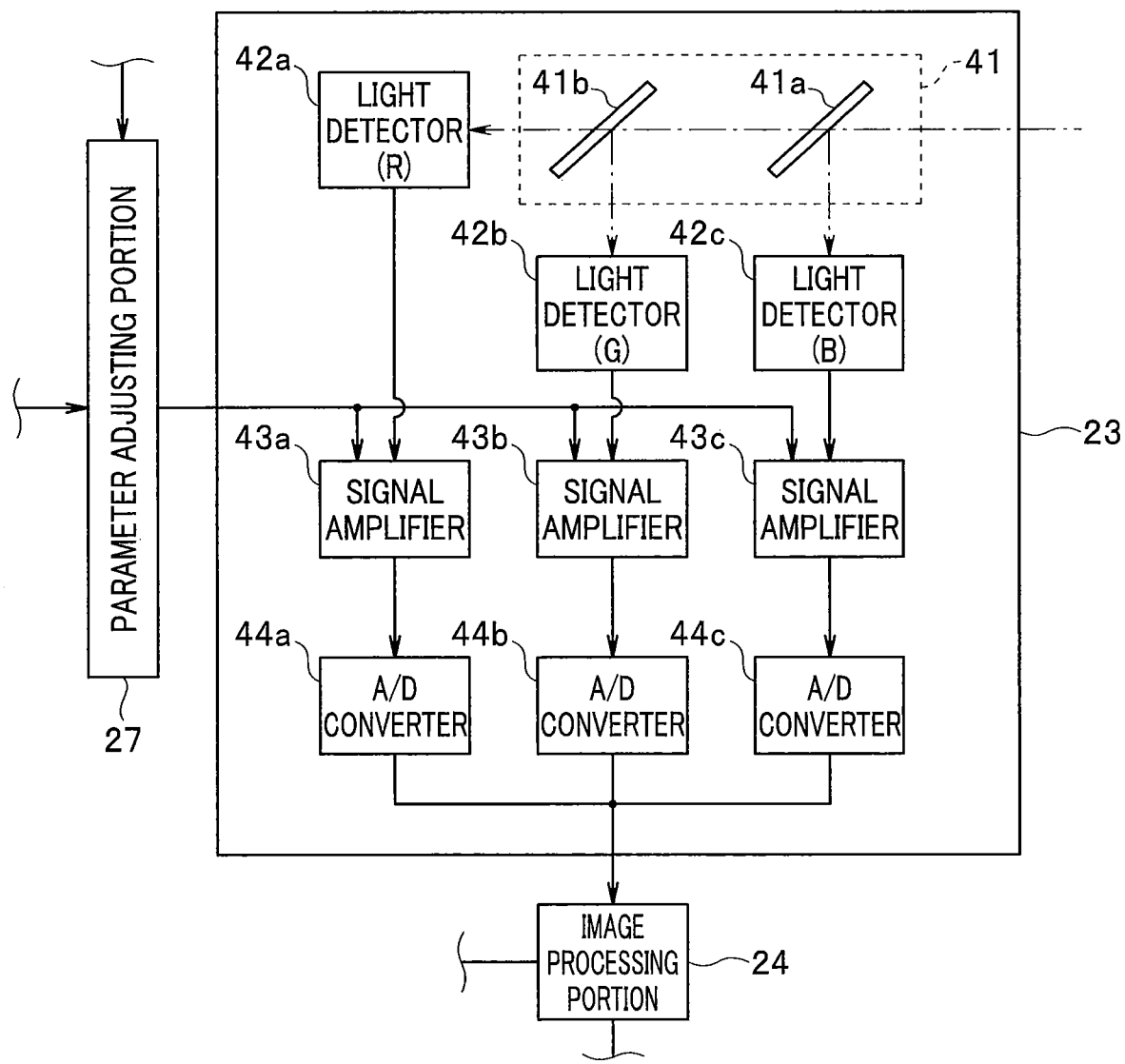
FIG. 2 is a diagram showing an example of a configuration of a light detecting portion according to the first embodiment.

The light detecting portion 23 is configured to detect light caused to be incident via the connector receiving portion 62 to generate an electric signal, amplify the generated electric signal, and generate a digital signal indicating a luminance value corresponding to the amplified electric signal to output the digital signal to the image processing portion 24. More specifically, the light detecting portion 23 is configured having, for example, a spectroscopic optical system 41 provided with dichroic mirrors 41a and 41b, light detectors 42a to 42c, signal amplifiers 43a to 43c and A/D converters 44a to 44c as shown in FIG. 2. FIG. 2 is a diagram showing an example of a configuration of a light detecting portion according to the first embodiment.

The dichroic mirror 41a is configured being provided with such an optical characteristic that causes R light and G light included in light caused to be incident via the connector receiving portion 62 to be transmitted to the dichroic mirror 41b side and causes B light included in the light to be reflected to the light detector 42c side.

The dichroic mirror 41b is configured being provided with such an optical characteristic that causes the R light caused to be incident via the dichroic mirror 41a to be transmitted to the light detector 42a side and causes the G light to be incident via the dichroic mirror 41a to be reflected to the light detector 42b side.

The light detector 42a is configured being provided with, for example, an avalanche photodiode or a photo multiplier tube. Further, the light detector 42a is configured to receive the R light caused to be incident via the dichroic mirror 41b with a predetermined sensitivity, and generate and output an electric signal corresponding to an amount of the received R light.

The light detector 42b is configured being provided with, for example, an avalanche photodiode or a photo multiplier tube. Further, the light detector 42b is configured to receive the G light reflected by the dichroic mirror 41b with a predetermined sensitivity, and generate and output an electric signal corresponding to an amount of the received G light.

The light detector 42c is configured being provided with, for example, an avalanche photodiode or a photo multiplier tube. Further, the light detector 42c is configured to receive the B light reflected by the dichroic mirror 41a with a predetermined sensitivity, and generate and output an electric signal corresponding to an amount of the received B light.

The signal amplifier 43a is configured to amplify an electric signal outputted from the light detector 42a with an amplification factor adjusted by the parameter adjusting portion 27 and output the electric signal.

The signal amplifier 43b is configured to amplify an electric signal outputted from the light detector 42b with an amplification factor adjusted by the parameter adjusting portion 27 and output the electric signal.

The signal amplifier 43c is configured to amplify an electric signal outputted from the light detector 42c with an amplification factor adjusted by the parameter adjusting portion 27 and output the electric signal.

The A/D converter 44a is configured to have a predetermined input voltage range. Further, the A/D converter 44a is configured to convert an electric signal outputted from the signal amplifier 43a to a gradation signal graded so as to have a predetermined number of bits (hereinafter also referred to simply as a digital signal) and output the gradation signal.

The A/D converter 44b is configured to have a predetermined input voltage range. Further, the A/D converter 44b is configured to convert an electric signal outputted from the signal amplifier 43b to a digital signal and output the digital signal.

The A/D converter 44c is configured to have a predetermined input voltage range. Further, the A/D converter 44c is configured to convert an electric signal outputted from the signal amplifier 43c to a digital signal and output the digital signal.

The image processing portion 24 is configured being provided with, for example, an image processing circuit such as an AGC (auto gain control) circuit 24a. Further, the image processing portion 24 is configured to generate an image of an object by detecting a scan pattern of the object based on a drive signal outputted from the scan control portion 22, mapping luminance values indicated by a digital signal outputted from the light detecting portion 23 to pixels at positions corresponding to the detected scan pattern, and performing interpolation processing for interpolating pixel information of each pixel excluded from mapping targets. Further, the image processing portion 24 is configured to output the image of the object generated as described above to the light adjusting portion 25. Further, the image processing portion 24 is configured to generate a display image by performing processing such as gain adjustment by the AGC circuit 24a for the image of the object generated as described above and output the generated display image to the display apparatus 4.

The light adjusting portion 25 is configured being provided with, for example, a light-adjusting circuit. Further, the light adjusting portion 25 is configured, for example, so as to calculate an average value of luminance values of an image outputted from the image processing portion 24, generate a light adjustment signal for causing a difference between the calculated average value of the luminance values and a predetermined brightness target value to be close to zero and output the generated adjustment signal to the light source control portion 28.

The memory 26 stores an output upper limit value Pmax and an output lower limit value Pmin of the light sources 31a to 31c; a maximum gain value Mmax and a minimum gain value Mmin of the AGC circuit 24a, a transmittance C of the multiplexer 32, a transmittance U of the connector portion 61 and the connector receiving portion 62, a sensitivity Q of light detectors 42a to 42c, the number of increased gradations A indicating the increased number of gradation values for each 1 volt for the input voltage range (full-scale) of the A/D converters 44a to 44c, and a median So of the number of gradations indicated by a digital signal generated by the A/D converters 44a to 44c.

The output upper limit value Pmax is, for example, a fixed value expressed in milliwatt and set based on a specified value of AEL (accessible emission limit) provided in IEC60825, which is an international standard which provides a safety criteria for laser products. Further, the output upper limit value Pmax is set as a value corresponding to each of the light sources 31a to 31c.

The output lower limit value Pmin is, for example, a fixed value expressed in milliwatt and set as a value making it possible to maintain emission of laser from the light sources 31a to 31c. Further, the output lower limit value Pmin is set as a value corresponding to each of the light sources 31a to 31c.

The maximum gain value Mmax and the minimum gain value Mmin are set as dimensionless fixed values used in gain adjustment by the AGC circuit 24a.

Each of the transmittance C and the transmittance U is set, for example, as a dimensionless fixed value between 0 and 1, including 0 and 1. Further, each of the transmittance C and the transmittance U is set as a value corresponding to each of R light, G light and B light.

The sensitivity Q is, for example, a value expressed in the number of volts for each 1 milliwatt (V/mW) and set as a fixed value corresponding to each of light detectors 42a to 42c.

The number of increased gradations A is set, for example, as a fixed value corresponding to each of the A/D converters 44a to 44c. More specifically, for example, if the A/D converter 44b has an input voltage range of 0 to 10 volts, and a digital signal expressed in 4096 gradations from 0 to 4095 (12 bits) is outputted from the A/D converter 44b, the number of increased gradations A of the A/D converter 44b is set as 409.6.

The median So is set as a fixed value common to the A/D converters 44a to 44c. More specifically, if digital signals expressed in 4096 gradations from 0 to 4095 (12 bits) are outputted from the A/D converters 44a to 44c, the value of the median So is set as 2047.

The parameter adjusting portion 27 is configured being provided with, for example, a CPU.

The parameter adjusting portion 27 is configured to read the optical characteristic information stored in the memory 16 when the connector portion 61 and the connector receiving portion 62 are connected. Further, the parameter adjusting portion 27 is configured to adjust an amplification factor G corresponding to each of the signal amplifiers 43a to 43c based on each value included in the optical characteristic information read from the memory 16 and each value stored in the memory 26. Note that details of a method for adjusting the amplification factor G corresponding to each of the signal amplifiers 43a to 43c will be described later.

The light source control portion 28 is configured being provided with, for example, a CPU or a control circuit.

The light source control portion 28 is configured to be capable of performing control for separately switching the light sources 31a to 31c between the on state and the off state.

The light source control portion 28 is configured to set a corresponding minimum drive current value Imin for each of the light sources 31a to 31c based on the output lower limit value Pmin stored in the memory 26. Further, the light source control portion 28 is configured to set a corresponding maximum drive current value Imax for each of the light sources 31a to 31c based on the output upper limit value Pmax stored in the memory 26. Further, the light source control portion 28 is configured to be capable of causing an amount of light for each of R light, G light and B light to change by fluctuating a current value of a drive current supplied to the light sources 31a to 31c within a range from the minimum drive current value Imin to the maximum drive current value Imax, the current values Imin and Imax being set as described above, based on a light amount detection signal outputted from the light amount detecting portion 12A and a light adjustment signal outputted from the light adjusting portion 25.

Next, operation of the present embodiment will be described.

Note that, hereinafter, description will be made on an assumption that a light amount loss of each of an optical path of light emitted from the multiplexer 32 to the connector receiving portion 62, an optical path of light emitted from the connector receiving portion 62 to the light detecting portion 23, the condensing optical system 14 and the spectroscopic optical system 41 is 0 or slight, for simplification.

Further, in the present embodiment, a common adjustment method can be used as a method for adjusting an amplification factor Gr of the signal amplifier 43a, an amplification factor Gg of the signal amplifier 43b and an amplification factor Gb of the signal amplifier 43c. Therefore, hereinafter, description will be made on a case of adjusting the amplification factor Gg of the signal amplifier 43b as a representative example.

Further, hereinafter, description will be made on an assumption that optical characteristic information which includes a transmittance T1g of G light for the illumination fiber 12, light receiving efficiency Leg of the G light, and a transmittance T2g of the G light for the light receiving fibers 13 is stored in the memory 16.

Further, hereinafter, description will be made on an assumption that an output upper limit value Pgmax and output lower limit value Pgmin of the light source 31b, a transmittance Cg of G light for the multiplexer 32, a transmittance Ug of the G light for the connector portion 61 and the connector receiving portion 62, a sensitivity Qg of the G light for the light detector 42b, and the number of increased gradations Ag indicating the increased number of gradation values for each 1 volt for the input voltage range of the A/D converter 44b are stored in the memory 26.

In the present embodiment, by performing gain adjustment by the AGC circuit 24a for a luminance value indicated by a digital signal outputted from the light detecting portion 23 in response to receiving of G light, a luminance value Sg after the gain adjustment is acquired in real time. Therefore, for example, when a current output value of the light source 31b is indicated by Pg, and a current gain value of the AGC circuit 24a is indicated by M, the luminance value Sg after the gain adjustment can be expressed like a following equation (1). Note that, in the present embodiment, it is assumed that a luminance value for a display image to be displayed on the display apparatus 4 is obtained by rounding processing such as rounding off being performed for values below a decimal point of the luminance value Sg after the gain adjustment.

$$Sg = Pg \cdot Cg \cdot Ug \cdot T1g \cdot Leg \cdot T2g \cdot Qg \cdot Gg \cdot Ag \cdot M \quad (1)$$

That is, according to the above equation (1), it is possible to perform such brightness adjustment that the luminance value Sg is adjusted to be of a magnitude suitable for observation by changing a combination of the output value Pg and a gain value M. Further, according to the above equation (1), even if each of the output value Pg and the gain value M is a constant value, a different luminance value Sg corresponding to a magnitude of each of values of the transmittance T1g, the light receiving efficiency Leg and the transmittance T2g is acquired.

Further, according to the above equation (1), for example, in a case where each of a range from the output upper limit value Pgmax to the output lower limit value Pgmin corresponding to an output value Pg variable range and a range from the maximum gain value Mmax to the minimum gain value Mmin, corresponding to a gain value M variable range is narrow, a situation may happen in which it is impossible to acquire a preferable luminance value Sg no matter how the output value Pg and the gain value M are adjusted.

Therefore, according to the present embodiment, the parameter adjusting portion 27 adjusts the amplification factor Gg of the signal amplifier 43b so that a condition shown by a following equation (2) is satisfied, based on each value read from the memory 16 of the endoscope 2 connected to the body apparatus 3 and each value stored in the memory 26.

$$\{(Pgmax \cdot Mmax + Pgmin \cdot Mmin) \\ Cg \cdot Ug \cdot T1g \cdot Leg \cdot T2g \cdot Qg \cdot Gg \cdot Ag\}/2 = So \quad (2)$$

That is, by adjusting the amplification factor Gg of the signal amplifier 43b so that the condition of the above equation (2) is satisfied, for example, the output value Pg is adjusted so as to be a median Pc within the output value Pg variable range, the gain value M is adjusted so as to be a median Mc within the gain value M variable range, and, furthermore, a luminance value Sg corresponding to the median So can be acquired when an object is observed at a standard observation distance for the endoscope 2.

As described above, according to the present embodiment, it is possible to, for example, even if each of the output value Pg variable range and the gain value M variable range is narrow, adjust the output value Pg and the gain value M so that a favorable luminance value Sg can be obtained, irrespective of the magnitude of each of the values of the transmittance T1g, the light receiving efficiency Leg and transmittance T2g. Therefore, according to the present embodiment, it is possible to perform brightness adjustment favorable for each endoscope even in a case of switching among a plurality of endoscopes the magnitudes of light amount loss of which are mutually different.

Note that, according to the present embodiment, since it is possible to, for example, in a case where the output lower limit value Pgmin is sufficiently smaller in comparison with the output upper limit value Pgmax, cause a resultant value of multiplication of the output lower limit value Pgmin and the minimum gain value Mmin in the above equation (2) to be 0, the amplification factor Gg of the signal amplifier 43b may be adjusted so that a condition shown by a following equation (3) is satisfied.

$$\{(Pgmax \cdot Mmax \cdot Cg \cdot Ug \cdot T1g \cdot Leg \cdot T2g \cdot Qg \cdot Gg \cdot Ag\}/2 = So \quad (3)$$

Figure 3:
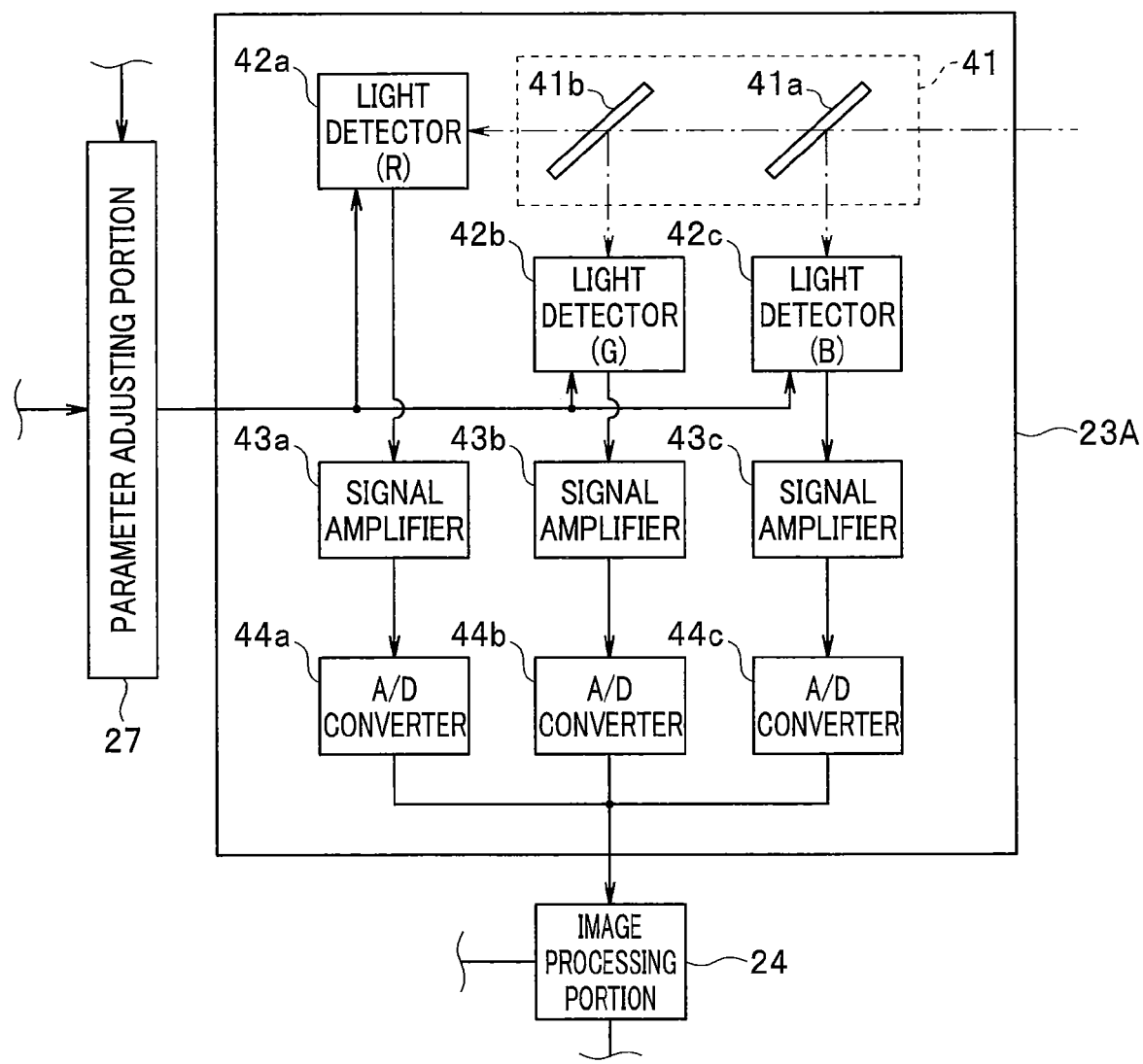
FIG. 3 is a diagram showing an example of the configuration of the light detecting portion according to the first embodiment, which is different from the example in FIG. 2.

On the other hand, according to the present embodiment, for example, a light detecting portion 23A provided with a function substantially similar to that of the light detecting portion 23, as shown in FIG. 3 may be provided to constitute the endoscope system 1. FIG. 3 is a diagram showing an example of the configuration of the light detecting portion according to the first embodiment, which is different from the example in FIG. 2.

In the light detecting portion 23A, each of the amplification factor G and the number of increased gradations A is set as a fixed value, while the sensitivity Q is adjusted by the parameter adjusting portion 27.

Further, in the case of providing the light detecting portion 23A to constitute the endoscope system 1, the output upper limit value Pmax and the output lower limit value Pmin, the maximum gain value Mmax and the minimum gain value Mmin, the transmittance C, the transmittance U, the amplification factor G, the number of increased gradations A and the median So are stored in the memory 26.

In the case of providing the light detecting portion 23A to constitute the endoscope system 1, the parameter adjusting portion 27 can adjust the sensitivity Qg of the light detector 42b so that the condition shown by the above equation (2) is satisfied, based on each value read from the memory 16 of the endoscope 2 connected to the body apparatus 3 and each value stored in the memory 26, and, furthermore, adjust each of a sensitivity Qr of the light detector 42a and a sensitivity Qb of the light detector 42c using a method similar to the adjustment method for the sensitivity Qg.

Note that each of the sensitivities Qr, Qg and Qb is defined, for example, as a value obtained by multiplying quantum efficiency, a multiplication factor and current/voltage conversion efficiency corresponding to each light detector. Therefore, the parameter adjusting portion 27 can adjust each of the sensitivities Qr, Qg and Qb, for example, by adjusting each of the multiplication factors of light detectors 42a to 42c. According to such an adjustment method, for example, it is possible to increase the sensitivity Qg by increasing the multiplication factor of the light detector 42b, and it is possible to decrease the sensitivity Qg by decreasing the multiplication factor of the light detector 42b.

Figure 4:
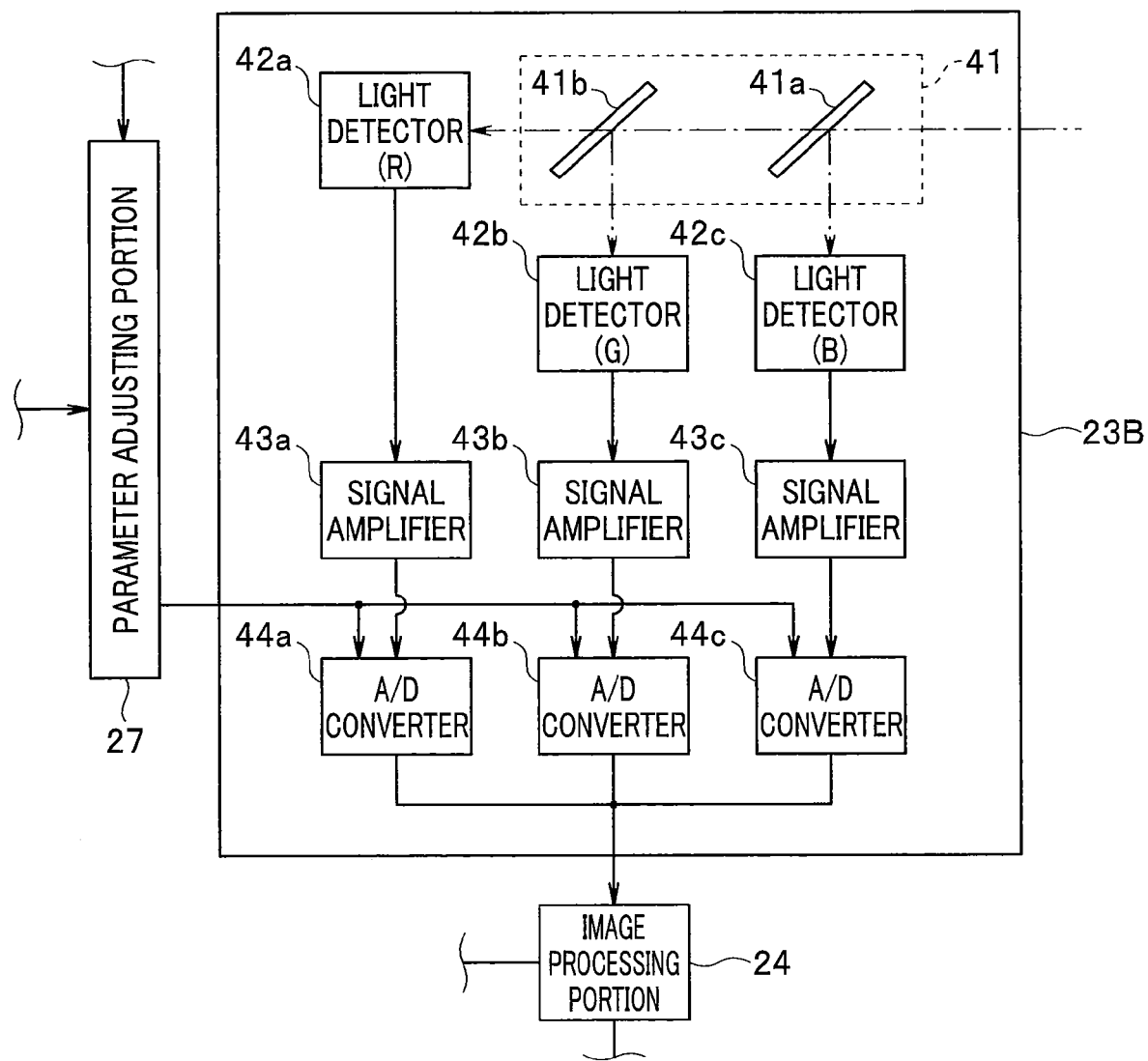
FIG. 4 is a diagram showing an example of the configuration of the light detecting portion according to the first embodiment, which is different from the examples in FIGS. 2 and 3.

Further, according to the present embodiment, instead of the light detecting portion 23, for example, a light detecting portion 23B provided with a function substantially similar to that of the light detecting portion 23, as shown in FIG. 4, may be provided to constitute the endoscope system 1. FIG. 4 is a diagram showing an example of the configuration of the light detecting portion according to the first embodiment, which is different from the examples in FIGS. 2 and 3.

In the light detecting portion 23B, each of the sensitivity Q and the amplification factor G is set as a fixed value, while the number of increased gradations A is adjusted by the parameter adjusting portion 27.

Further, in the case of providing the light detecting portion 23B to constitute the endoscope system 1, the output upper limit value Pmax and the output lower limit value Pmin, the maximum gain value Mmax and the minimum gain value Mmin, the transmittance C, the transmittance U, the sensitivity Q, the amplification factor G and the median So are stored in the memory 26.

In the case of providing the light detecting portion 23B to constitute the endoscope system 1, the parameter adjusting portion 27 can adjust the number of increased gradations Ag of the A/D converter 44b so that the condition shown by the above equation (2) is satisfied, based on each value read from the memory 16 of the endoscope 2 connected to the body apparatus 3 and each value stored in the memory 26, and, furthermore, adjust each of the number of increased gradations Ar of the A/D converters 44a and the number of increased gradations Ab of the A/D converter 44c using a method similar to the adjustment method for the number of increased gradations Ag.

Note that the parameter adjusting portion 27 can adjust each of the numbers of increased gradations Ar, Ag and Ab, for example, by adjusting the input voltage ranges of the A/D converters 44a to 44c. According to such an adjustment method, for example, it is possible to increase the number of increased gradations Ag by reducing the input voltage range of the A/D converter 44b, and it is possible to decrease the number of increased gradations Ag by expanding the input voltage range of the A/D converter 44b.

Further, according to the present embodiment, in a case where the memory 16 is not provided in the endoscope 2, for example, an adjustment method may be applied in which light of the output upper limit value Pmax is radiated to a predetermined object arranged at the standard observation distance of the endoscope 2, reflected light from the predetermined object is received, an average luminance value Sa of an image before gain adjustment, which is generated in response to the received reflected light and amplification factors Gt of the signal amplifiers 43a to 43c when the luminance value Sa is obtained are separately associated and stored into the memory 26, and the amplification factors of the signal amplifiers 43a to 43c when an average luminance value of the image after gain adjustment is Sa are adjusted to be Gt. Further, according to the present embodiment, white balance adjustment may be performed together with the acquisition of the average luminance value Sa described above.

Second Embodiment

Figure 5:
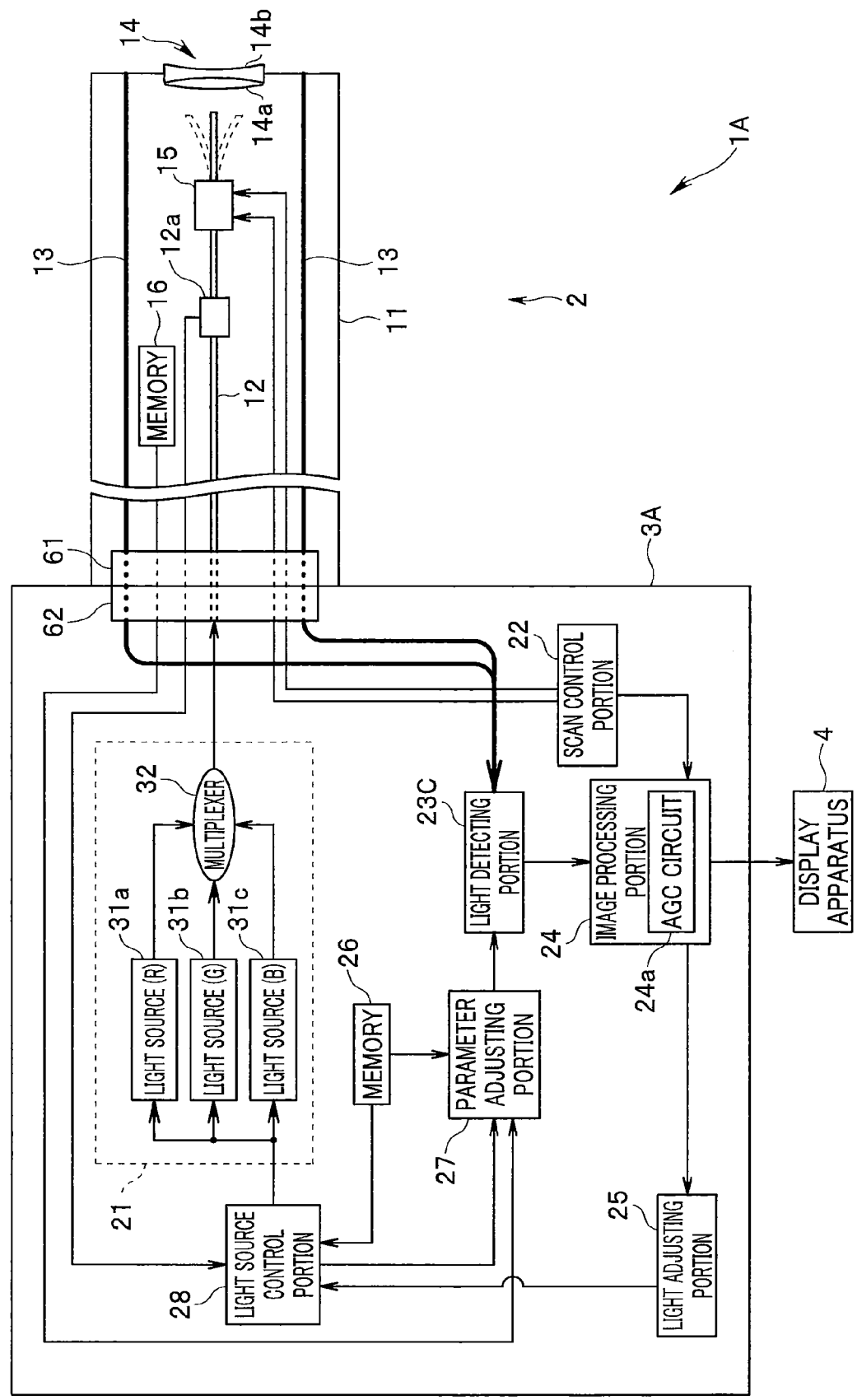
FIG. 5 is a diagram showing a configuration of main portions of an endoscope system according to a second embodiment.
Figure 6:
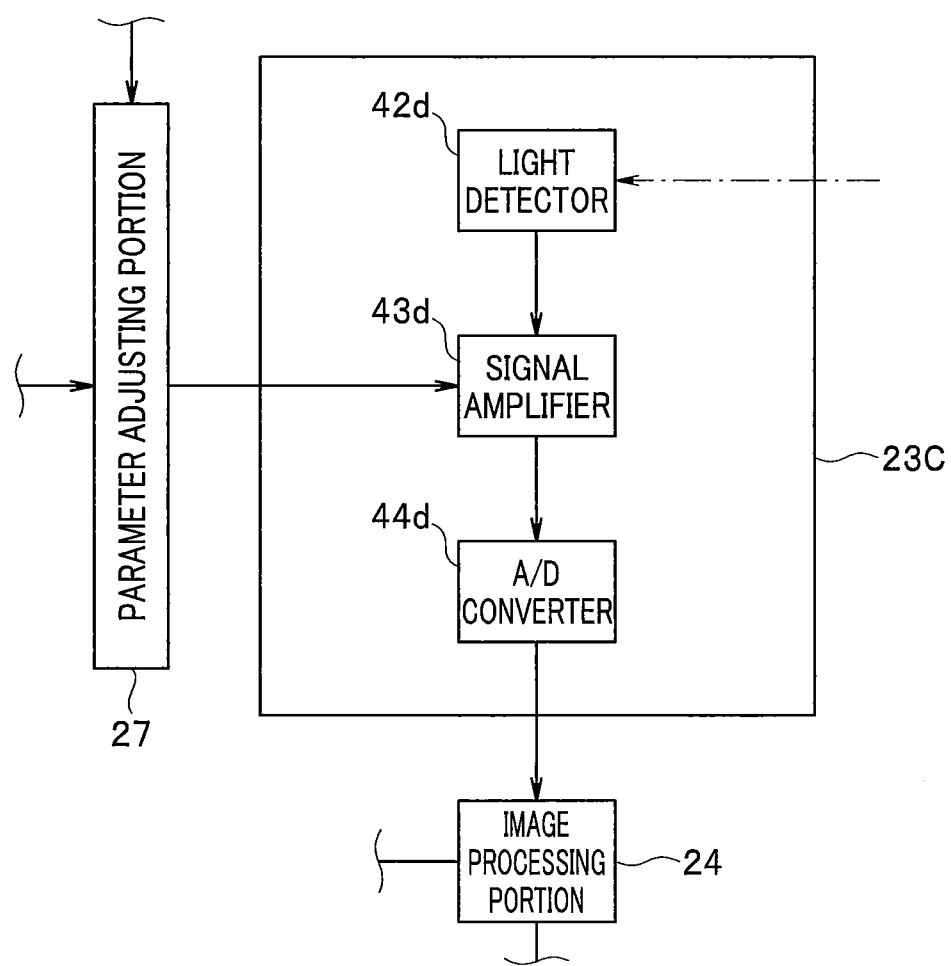
FIG. 6 is a diagram showing an example of a configuration of a light detecting portion according to the second embodiment.

FIGS. 5 and 6 relate to a second embodiment of the present invention. FIG. 5 is a diagram showing a configuration of main portions of an endoscope system according to the second embodiment.

Note that, in the present embodiment, detailed description about portions having configurations and the like similar to those of the first embodiment will be omitted, and description will be made mainly on portions having configurations and the like different from those of the first embodiment.

For example, as shown in FIG. 5, an endoscope system 1A is configured having the endoscope 2, a body apparatus 3A to which the endoscope 2 can be connected, and the display apparatus 4 to be connected to the body apparatus 3A.

The body apparatus 3A is configured having the light source portion 21, the scan control portion 22, the light detecting portion 23C, the image processing portion 24, the light adjusting portion 25, the memory 26, the parameter adjusting portion 27 and the light source control portion 28.

A light detecting portion 23C is configured to detect light caused to be incident via the connector portion 61 and the connector receiving portion 62, generate a digital signal indicating a luminance value corresponding to an amount of the detected light and output the generated digital signal to the image processing portion 24. More specifically, as shown in FIG. 6, the light detecting portion 23C is configured having, for example, a light detector 42d, a signal amplifier 43dc and an A/D converter 44d. FIG. 6 is a diagram showing an example of a configuration of a light detecting portion according to the second embodiment.

The light detector 42d is configured being provided with, for example, an avalanche photodiode or a photo multiplier tube. Further, the light detector 42d is configured to receive light caused to be incident via the connector receiving portion 62, and generate and output an electric signal corresponding to an amount of the received light.

The signal amplifier 43d is configured to amplify an electric signal outputted from the light detector 42d with an amplification factor adjusted by the parameter adjusting portion 27 and output the electric signal.

The A/D converters 44d is configured to convert an electric signal outputted from the signal amplifier 43d to a digital signal and output the digital signal.

The light source control portion 28 of the present embodiment is configured, for example, to perform operation for causing pulse-shaped R light, G light and B light to be emitted in that order, while switching among the R light, G light and B light at each predetermined time interval T. Further, the light source control portion 28 of the present embodiment is also configured to generate a synchronization signal having a waveform or the like from which an R light emission timing, a G light emission timing and a B light emission timing can be separately identified, and output the synchronization signal to the parameter adjusting portion 27.

The parameter adjusting portion 27 of the present embodiment is configured to adjust an amplification factor of the signal amplifier 43d at the R light emission timing to Gr1, adjust the amplification factor of the signal amplifier 43d at the G light emission timing to Gg1 and adjust the amplification factor of the signal amplifier 43d at the B light emission timing to Gb1, based on each value included in optical characteristic information read from the memory 16, each value stored in the memory 26 and the synchronization signal outputted from the light source control portion 28.

Note that, as for a method for adjusting the amplification factors Gr1, Gg1 and Gb1, a method similar to the method for adjusting the amplification factors Gr, Gg and Gb already described in the first embodiment is applicable, and, therefore, description will be omitted.

Therefore, according to the present embodiment, it is possible to perform brightness adjustment favorable for each endoscope even in a case of switching among a plurality of endoscopes the magnitudes of light amount loss of which are mutually different.

Note that the present invention is not limited to each embodiment described above, and various modifications and applications are, of course, possible within a range not departing from the spirit of the present invention.

What is claimed is:
1. An image processing system comprising:
one or more light receiving optical members configured to guide return light from an object to which illuminating light emitted by one or more light sources is radiated, wherein the illuminating light has a current value within a variable range of output power;
a light detecting portion comprising:
a light detector configured to receive the return light guided by the one or more light receiving optical members and incident on the light detector, and to perform a generation process to generate an electric signal based on the return light;
a signal amplifier configured to perform an amplification process to amplify the electric signal and output an amplified electrical signal; and an analog to digital converter configured to perform a conversion process to convert the amplified electric signal to a digital signal and output the digital signal; and one or more processors comprising hardware, wherein the one or more processors are configured to:

generate a current image based on the digital signal outputted from the analog to digital converter;

perform gain adjustment of the current image by a current gain value within a variable range of gains; and adjust a predetermined parameter of at least one of the generation process of the light detector, the amplification process of the signal amplifier and the conversion process of the analog to digital converter based on the current value of the illuminating light within the variable range of output power and the current gain value within the variable range of gains so that a luminance value of a subsequent image generated after the current image based on subsequently received return light received by the light detector is a predetermined luminance value.

2. The image processing system according to claim 1, wherein the one or more processors are configured to:

retrieve, from a storage, optical characteristic information including light receiving efficiency at time of the one or more light receiving optical members guiding the subsequently received return light; and adjust the predetermined parameter based on the current value of the illuminating light within the variable range of output power, the current gain value within the variable range of gains, and the optical characteristic information so that the luminance value of the subsequent image is the predetermined luminance value.

3. The image processing system according to claim 1, wherein the one or more light sources are configured to separately emit first light and second light having a wavelength band different from a wavelength band of the first light as the illuminating light, and wherein the one or more processors are configured to:

perform control of the one or more light sources to cause the first light and the second light to be emitted from the one or more light sources while switching between the first light and the second light at each predetermined time interval; and separately adjust the predetermined parameter at a timing of emitting the first light and at a timing of emitting the second light.

4. The image processing system according to claim 2, wherein the one or more processors are configured to adjust the predetermined parameter based on the current value of the illuminating light within the variable range of output value, the current gain value within the variable range of gains, and the optical characteristic information so that the luminance value of the subsequent image is a predetermined target value at a median in the variable range of output value and a median of the variable range of gains.

5. The image processing system according to claim 4, wherein the predetermined target value is a luminance value corresponding to a median of a number of gradations indicated by the digital signal.

6. The image processing system according to claim 5, wherein the predetermined parameter is a light receiving sensitivity of the light detector at time of the light detector receiving the subsequently received return light and generating a subsequent electric signal based on the subsequently received return light.

7. The image processing system according to claim 5, wherein the light detector is configured to generate a subsequent electric signal based on the subsequently received return light, and wherein the predetermined parameter is an amplification factor of the signal amplifier at time of amplifying the subsequent electric signal generated by the light detector.

8. The image processing system according to claim 5, wherein the light detector is configured to generate a subsequent electric signal based on the subsequently received return light, wherein the signal amplifier is configured to amplify the subsequent electric signal and output a subsequent amplified electric signal, and wherein the predetermined parameter is an input voltage range of the analog to digital converter at time of converting the subsequent amplified electric signal to a subsequent digital signal.

9. The image processing system according to claim 2, further comprising an endoscope provided with an illumination optical member configured to guide the illuminating light emitted from the one or more light sources and radiating the illuminating light to the object, wherein optical characteristic information further includes a spectral transmittance of the illumination optical member.

10. The image processing system according to claim 1, further comprising the one or more light sources.

* * * * *